United States Patent [19]
Gold et al.

[11] Patent Number: 5,042,951
[45] Date of Patent: Aug. 27, 1991

[54] HIGH RESOLUTION ELLIPSOMETRIC APPARATUS

[75] Inventors: Nathan Gold, Redwood City; David L. Willenborg, Dublin; Jon Opsal, Livermore; Allan Rosencwaig, Danville, all of Calif.

[73] Assignee: Therma-Wave, Inc., Fremont, Calif.

[21] Appl. No.: 409,393

[22] Filed: Sep. 19, 1989

[51] Int. Cl.⁵ .................................................. G01J 4/00
[52] U.S. Cl. .................................... 356/369; 356/364; 356/381
[58] Field of Search ............ 356/369, 364, 381, 382, 356/367, 351; 250/225

[56] References Cited

U.S. PATENT DOCUMENTS

| | | | |
|---|---|---|---|
| 3,836,787 | 9/1974 | Ash | 356/369 |
| 4,472,633 | 9/1984 | Motooka | 250/338 |
| 4,516,855 | 5/1985 | Korth | 356/347 |
| 4,585,348 | 4/1986 | Chastang et al. | 356/369 |
| 4,647,207 | 3/1987 | Bjork et al. | 356/369 |
| 4,650,335 | 3/1987 | Ito et al. | 356/369 |
| 4,653,924 | 3/1987 | Itonaga et al. | 356/369 |
| 4,655,595 | 4/1987 | Bjork et al. | 356/369 |
| 4,725,145 | 2/1988 | Azzam | 356/367 |
| 4,762,414 | 8/1988 | Grego | 356/349 |
| 4,790,659 | 12/1988 | Erman et al. | 356/369 |

FOREIGN PATENT DOCUMENTS 0147606  8/1985  Japan ................................. 356/381
0259446  10/1988  Japan ................................. 356/369

OTHER PUBLICATIONS

Lasers in Industry, edited by S. S. Charschan, Member of Research Staff, Western Electric Van Nostrand Reinhold Company, 1972, pp. 326-334.
Ellipsometry and Polarized Light, R. M. Azzam and N. M. Bashara, North Holland Physics Publishing, 1988; pp. 233-268 & 320-332.

Primary Examiner—Richard A. Rosenberger
Assistant Examiner—Hoa Pham
Attorney, Agent, or Firm—Limbach, Limbach & Sutton

[57] ABSTRACT

In an ellipsometric apparatus, a laser is provided for generating a probe beam. The probe beam is passed through a polarization section to give the beam a known polarization state. The probe beam is then tightly focused with a high numerical aperture lens onto the surface of the sample. The polarization state of the reflected probe beam is analyzed. In addition, the angle of incidence of one or more rays in the incident probe beam is determined based the radial position of the rays within the reflected probe beam. This approach provides enhanced spatial resolution and allows measurement over a wide spread of angles of incidence without adjusting the position of the optical components. Multiple angle of incidence measurements are greatly simplified.

24 Claims, 3 Drawing Sheets

HIGH RESOLUTION ELLIPSOMETRIC APPARATUS

TECHNICAL FIELD

The subject invention relates to a high resolution ellipsometric apparatus for studying physical properties of a sample.

BACKGROUND OF THE INVENTION

Ellipsometry is a nondestructive technique for studying the physical properties of a sample based on changes induced in the polarization state of a light beam interacting with the sample. In all ellipsometer systems, a light beam having a known polarization state is reflected from or transmitted through the sample. The polarization state of the beam after it interacts with the sample is then measured. The differences in the polarization state of the beam before and after the interaction with the sample can be used to calculate parameters of the sample. In the subject application, the term polarization state is intended to mean the respective amplitudes and phase difference between the p and s polarization components.

The most common form of ellipsometry is reflection ellipsometry where a light beam is directed at an oblique angle of incidence to the sample surface. The polarization state of the reflected beam is measured to derive information about the surface of the material. Common parameters which are studied include the index of refraction and extinction coefficient of the sample. More recently, reflection ellipsometry has been proposed to study carrier densities in a semiconductor wafer (See U.S. Pat. No. 4,472,663, issued Sept. 18, 1984 to Motooka). The most common industry use for ellipsometers is in the characterization of thin film layers on semiconductor samples. Reflection ellipsometry is the best method available for measuring the thickness of very thin layers on semiconductors.

It is also possible to use ellipsometric techniques to analyze a light beam which is transmitted through a sample. This method is referred to as transmission ellipsometry or polarimetry. As in reflection ellipsometry, the polarization state of the incoming beam is compared to the polarization state of the beam after it has passed through the sample. Polarimetry is used to study bulk properties of transparent materials such as the birefringence of crystals. For the sake of simplicity, the discussion in the remainder of this application will be limited to reflection ellipsometry, however the subject invention is applicable to both reflection and transmission ellipsometry.

Turning to FIG. 1, there is illustrated the basic form of a prior art ellipsometer for evaluating the parameters of a sample 10. As shown therein, a means, such as laser 12, generates a beam of radiation 14. This beam is passed through a polarizing section 16 for creating a known polarization state of the beam. The polarization section 16 can include one or more components which will be discussed below. The beam is then reflected off the sample at an oblique angle of incidence $\theta$ with respect to the normal N as shown in FIG. 1. The reflected beam is then passed through an analyzing section 18 for isolating the polarization state of the reflected beam. The intensity of the beam is then measured by a photodetector 20. A processor 22 can then be used to determine parameters of the sample 10 by comparing the polarization state of the input beam with the polarization state of the reflected beam.

There are a wide variety of ellipsometer schemes which have been developed in the prior art. A thorough discussion of many prior art systems can be found in the comprehensive text by R. M. A. Azzam and N. M. Bashara entitled, *Ellipsometry and Polarized Light*, North Holland Publishing Co., New York, NY, 1977. In the latter text, significant detail is provided as to the various types of optical components which can be used in the polarization and analyzing sections 16 and 18. Due to the non-directional nature of optical laws, the sequence in which these various optical components are disposed may be interchanged. Typically, the components utilized can include a linear or circular polarizer, a birefringent device often referred to as a compensator, and a linear or circular analyzer. In operation, one or more of these elements are rotated about the azimuth in a manner to vary the polarization state of the beam. Information about sample parameters is derived from the photodetector output as it relates to the azimuthal positions of the various elements.

One of the earliest developed ellipsometric methods is called null ellipsometry. In null ellipsometry, the change in state of polarization which is caused by the sample is compensated by suitable adjustment of the polarizing and analyzing sections such that the reflected light beam is extinguished by the analyzing section. More specifically, the azimuthal angle of the elements are rotated until a null or minimum level intensity is measured by the detector.

In a photometric ellipsometer, no effort is made to extinguish the light reaching the detector. Rather, the level of light intensity recorded by the detector is measured and compared with the azimuth angles of the components in the polarizing and analyzing sections to derive information about the sample. The processor utilizes mathematical models, including Fresnel equations, to determine the sample parameters. As described in detail in the Azzam and Bashara text, the mathematical models typically include a calculation for the "ellipsometric parameters" $\psi$ and $\delta$. These parameters are related to the relative magnitudes of the p and s polarization states of the reflected beam as well as the phase delay between those two polarizations by the following equations:

$$\frac{R_p}{R_s} = \tan \psi e^{i\delta} \tag{1}$$

$$\tan \psi = \left| \frac{R_p}{R_s} \right| \tag{2}$$

$$\delta = \arg\left(\frac{R_p}{R_s}\right) \tag{3}$$

There are many other ellipsometric techniques that are found in the prior art and will be mentioned briefly below. One such technique is modulated ellipsometry wherein small changes in the optical parameters of a surface that are induced by an external field are measured. (See, Azzam, page 265.) Another approach is interferometric ellipsometry. (See, Azzam, page 262 and in U.S. Pat. No. 4,762,414 issued Aug. 9, 1980 to Grego.) In another approach, the reflected probe beam is split into two or more beams and measured by different detectors (See, U.S. Pat. No. 4,585,384, issued Apr. 29, 1986 to Chastang.)

A new approach is disclosed in U.S. Pat. No. 4,725,145, issued Feb. 16, 1988 to Azzam. In the latter patent, the detector is arranged in a manner to simultaneously function as the analyzer section. More specifically, the detector is arranged to be polarization sensitive and has a partially specularly reflecting surface intended to isolate radiation of a certain polarization state. While the approach in Azzam reduces the number of components, the system is still like other prior art devices in that the polarization state of the reflected probe beam must be known. As will be seen below, the subject invention can be used to substantially improve any of the above described ellipsometric methods and apparatus.

As can be appreciated from the above discussion, each of the ellipsometric methods in the prior art require that the incoming beam strike the surface of the sample at an oblique angle of incidence. This has always been performed by directing the entire beam at an oblique angle with respect to the sample surface and having an independent detection system aligned with the reflected beam for capturing, analyzing and measuring the beam. This approach has some serious limitations. First of all, the beam generation and collection components must be accurately aligned. This alignment must be accurate as to both the angle of incidence and reflection of the beam and the azimuthal angles of the incoming beam. The term azimuthal angle in this sense relates to variations in and out of the plane of the paper of FIG. 1, rather than rotation about the direction of travel of the beam which is relevant when discussing the operation of the polarization and analyzing sections. Difficulties with alignment become extremely important in multiple angle of incidence ellipsometers which will be discussed in greater detail below.

As can be appreciated, alignment problems, while raising issues of complexity and cost, can at least be addressed. A more significant problem with the prior art devices that has not yet been solved arises from the need to direct the beam at an oblique angle of incidence which effectively limits spatial resolution. As used herein, resolution is intended to be a measure of the smallest area within which information can be derived. In the manufacturing of semiconductor devices, information about layer thicknesses within extremely small areas is extremely desirable. However, because of the need to direct the beam at an oblique angle of incidence, it is impossible to tightly focus the beam using high numerical aperture optics. Significant efforts have been made to improve the resolution of ellipsometers, but to date, spot sizes below 25 microns cannot be reliably achieved. As will be discussed below, the subject invention overcomes this problem and permits measurement of spot sizes on the order of 1 micron. Furthermore, the subject approach is self-aligning thereby substantially simplifying the measurement procedure.

There are a number of parameters which are used to define a semiconductor sample having a dielectric layer coated thereon. These parameters include the index of refraction and extinction coefficients of the air, thin-film layer and substrate, as well as the thickness of the thin-film layer. In practice, the extinction coefficients of the air and thin-film layer are negligible. However, this still leaves five sample parameters which can be unknown. In the ellipsometric devices described above, only two quantities $\psi$ and $\delta$ are measured and therefore only two of the five parameters can be ascertained such that the other three parameters must be known. In order to solve for more of the unknowns, additional independent measurements must be taken.

In the prior art, the need to obtain additional independent measurements has been addressed with multiple angle of incidence devices. (See, Azzam, page 320) In these devices, the angle of incidence of the beam is changed by varying the angular position of the laser generating components. Measurements are then taken at multiple angles of incidence. The multiple independent measurements allow additional unknown sample parameters to be calculated. Alternatively, the additional independent measurements can be used to calculate the unknown parameters with greater accuracy.

One of the drawbacks of multiple angle of incidence devices is that in order to measure the reflected beam, the angle of the detection components must also be similarly adjusted to capture the reflected beam. As can be appreciated, the need to adjust the position of all of the components makes accurate alignment even more difficult. As will be seen below, another important advantage of the subject invention is that multiple angle of incidence ellipsometry can be performed without adjusting the position of the beam generation or collection components.

Another problem with multiple angle of incidence devices is that they cannot be used to measure relatively shallow angles of incidence. As the thickness of the thin film increases, information from these shallow angles becomes of greater significance. As can be seen in FIG. 1, in order to obtain shallower angles of incidence, the light generating and collecting elements must be rotated up toward each other. The physical size and location of these components will make detection of angles of incidence of less that 20° quite difficult. As will be discussed below, an ellipsometer formed in accordance with the subject invention can measure multiple angles over a wide range, from 70° down to and including 0°.

Accordingly, it is an object of the subject invention to provide a new and improved ellipsometer configuration which is suitable for enhancing performance of all existing systems.

It is still another object of the subject invention to provide a new and improved ellipsometer with enhanced resolution.

It is still a further object of the subject invention to provide a new and improved ellipsometer which is self-aligning.

It is still another object of the subject invention to provide a new and improved ellipsometer which can provide multiple angle of incidence measurements without actively changing the angle of incidence the incoming beam.

It is still another object of the subject invention to provide a new and improved ellipsometer which is capable of determining multiple unknown parameters of a sample.

It is still a further object of the subject invention to provide an ellipsometer device coupled with a total power measurement for enhancing the calculation of sample parameters.

SUMMARY OF THE INVENTION

In accordance with these and many other objects. the subject invention provides for an ellipsometric apparatus and method for evaluating parameters of a sample. The subject ellipsometer includes a means for generating a probe beam of radiation having a known polarization state. The means for creating the known polarization state can be any of those found in the prior art.

Unlike the devices found in the prior art, wherein the probe beam is directed at an oblique angle to the sample, in the subject invention, the probe beam is directed substantially normal to the surface of the sample. The subject invention further includes a high numerical aperture lens for tightly focusing the probe beam to a relatively small spot on the surface of the sample. This tight focusing of the beam creates a spread of angles of incidence with respect to the sample surface of individual rays within the focused probe beam. The apparatus also includes a means for analyzing the polarization state of the probe beam after it has interacted with the sample. The means for analyzing the polarization state can include any of the components known in the prior art.

In addition to the known components, the analyzing means of the subject invention further includes a detector which functions to determine the angle of incidence with respect to the sample surface of various rays within the incident probe beam. The angle of incidence of these rays will depend on the radial position of the rays within the reflected probe beam. More specifically, the rays in the center of the beam represent the lowest angles of incidence while the radially outer rays within the reflected probe beam correspond to progressively higher angles of incidence. By comparing the polarization state of the incoming beam with that of the beam after it interacts with the sample, in relation to the angle of incidence, various parameters of the sample can be determined.

The approach used herein generates a high spread of angle of incidence without sacrificing the ability to tightly focus the beam. Moreover, the spread of angles of incidence allows multiple angle of incidence measurements to be made without adjusting the position of the components. Furthermore, since the reflected probe beam comes back up from the sample through the same focusing optics, the system is essentially self-aligning.

The concept of utilizing a high numerical aperture lens to gain high resolution as well as a large spread of angles of incidence with respect to the surface of the sample was first disclosed in applicants' co-pending application Ser. No. 07/347,812, filed May 4, 1989, assigned to the same assignee as the subject invention and incorporated herein by reference. In the device disclosed therein, the intensity of the reflected beam is measured as a function of the angle of incidence with respect to the surface of the sample to give information about film thickness. The latter case relies on the interference effects created when the beam is reflected off the sample. In contrast, in the subject invention, the change in polarization state induced in the beam as it reflects from the sample surface is measured. Accordingly, in the device described in the prior application, no specific measurement of the polarization state of the reflected beam was made. The approach described in the prior application can be extended to ellipsometry if the polarization state of both the incoming and reflected beams are measured as described herein.

The accuracy of measurement of the parameters of the sample in the subject device can be enhanced if the total reflected power of the probe beam is also measured. More specifically, it is known that the reflectivity of the surface of the sample will vary approximately sinusoidally as the thickness of the thin-film layer varies. Thus, unless the layer thickness is known to some degree, a specific thickness measurement cannot be derived from a reflectivity measurement alone since any specific measurement would be consistent with a number of different layer thicknesses. These ambiguities can be removed if a very good approximation of layer thickness is first made using an ellipsometric approach as described above. Once the ellipsometric measurement is made, additional data taken by measuring the total reflected power of the beam can be used to refine the measurement of layer thickness. This added sensitivity is a result of the fact that the signal to noise ratio of the measurement of the full power of the beam will be much better than the measurement where only portions of the beam, at discrete points corresponding to a specific angle of incidence are measured.

Further objects and advantages of the subject invention will be apparent from the following detailed description taken in conjunction with the drawings in which:

DETAILED DESCRIPTION OF THE PREFERRED EMBODIMENTS

Figure 1:
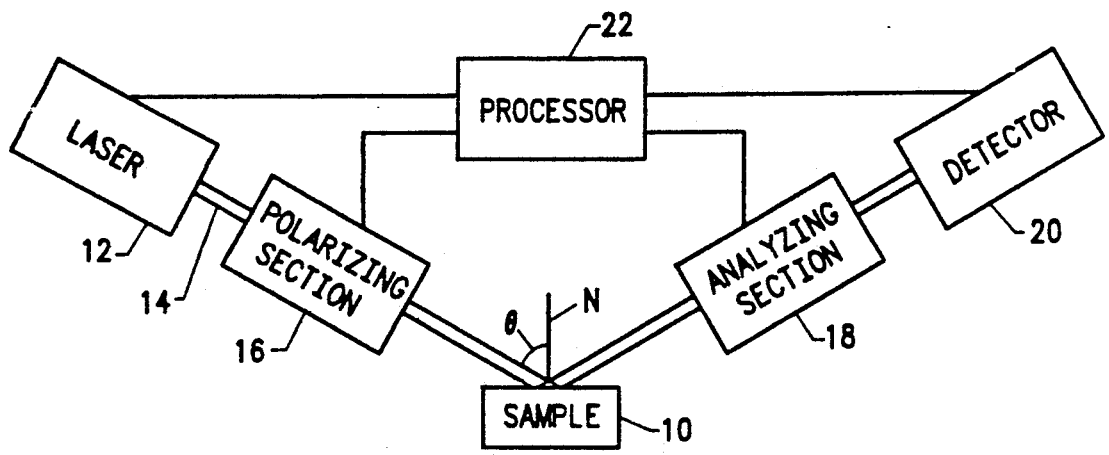
FIG. 1 is a simplified block diagram of a generalized form of a prior art ellipsometer device.
Figure 2:
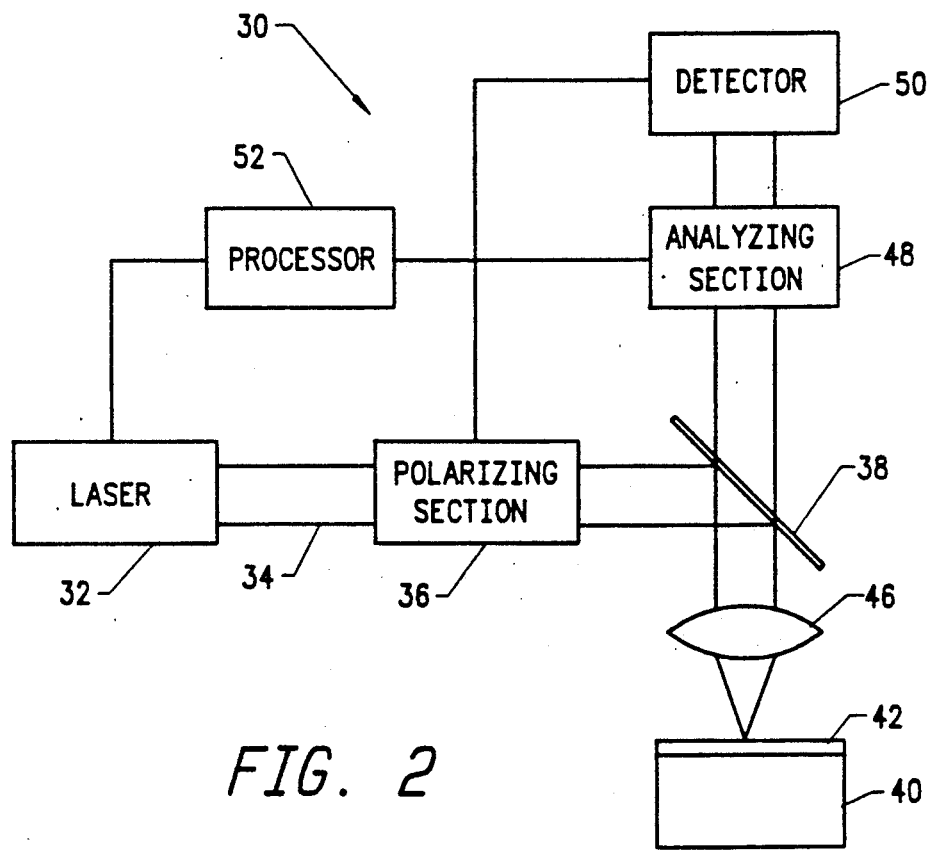
FIG. 2 is a simplified block diagram of an ellipsometer device formed in accordance with the subject invention.

Referring to FIG. 2, there is illustrated in schematic form, the basic apparatus 30 for carrying out the method of the subject invention. Apparatus 30 includes a laser 32 for generating a probe beam of radiation 34. The probe beam is passed through a polarization section 36 which can include any of the components known in the prior art. For example, polarizing section 36 can include a linear or circular polarizer and a birefringent quarter wave plate compensator. As is well known, certain lasers themselves are designed to emit light of a known polarization. Such a laser might be used to eliminate the need for a separate polarizer section 36. In either case, the combination of the laser and polarization section must result in a known polarization state for the probe beam 34.

After passing through the polarization section 36, the probe beam is reflected downward by a beam splitter 38 towards the sample 40 having a thin, optically transmissive film layer 42 thereon. As illustrated in FIG. 2, the beam is directed substantially normal to the surface of the sample. In accordance with the subject invention, beam 34 is tightly focused on the surface of the sample 40 with a high numerical aperture lens 46.

After the probe beam reflects off the surface of the sample it is reflected back up through beam splitter 38 into analyzer section 48. Once again, analyzer section 48 can include any of the components found in the prior art. For example, these components can include linear or circular polarizers and linear or circular analyzers. In a null ellipsometer configuration, the function of the polarization section and analyzing section is to introduce equal and opposite phase shifts to those caused by the reflection at the sample surface. By properly adjusting the components, the light reaching detector 50 can be minimized. Information about the position of the elements in the polarizing section and the analyzing section are supplied to a processor 52 for calculation of sample parameters by the methods used in the prior art. In a photometric approach, signal minimization is not required, and the output of the photodetector is compared with the azimuth angles of the various components in the polarization section and analyzer sections.

In accordance with the subject invention, the detector and processor are arranged such that information about the angle of incidence with respect to the sample surface of rays within the incident probe beam are determined based on the radial position of the rays within the reflected probe beam. The ability to extract this information can be appreciated by reference to FIGS. 3 and 4.

Figure 3:
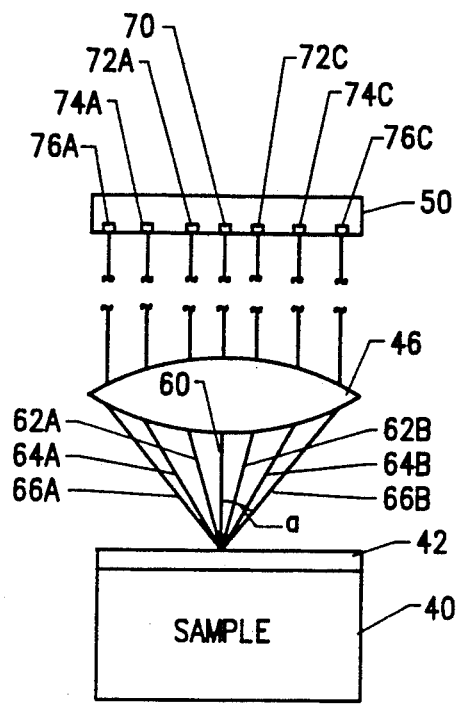
FIG. 3 is a diagram of a focused probe beam enlarged with respect to FIG. 1.

FIG. 3 illustrates lens 46 focusing the probe beam 34 on the sample 40. The reflected beam is shown impinging on detector 50. It should be noted that in FIG. 3, the beam splitter 38 and the analyzer section 48 have been omitted for clarity.

FIG. 3 also illustrates individual rays within the incident focused probe beam. As can be seen, where the beam 34 is directed substantially normal to the surface of the sample, the incident focused beam will include a center ray 60 substantially normal to the surface of the sample. The focused beam will also include outer rays 66A and B having a maximum angle $\theta_m$ of incidence with respect to the surface of the sample. (In three dimensions, rays 66A and B correspond to a cone of light.) The angle of incidence of the outer rays 66 are dependent upon the numerical aperture of lens 46. This maximum angle $\theta_m$ is given by the following equation:

$$\sin \theta_m = (numerical\ aperture). \quad (4)$$

Thus, the location of any ray in the reflected probe beam corresponds to the sine of the angle of incidence of the associated ray in the focused incident probe beam. For example, symmetric rays 64A and B illustrate an angle of 30° while symmetric rays 62A and B represent an angle of incidence of 15°.

Lens 46 is selected to have a high numerical aperture thereby maximizing the spread of angles of incidence. In practice, a lens creating a spread of angles (from the center ray to the outermost ray) of at least 30° is desired. A lens having a numerical aperture of 0.5 will provide such a spread of rays. In the preferred embodiment, a lens having a 0.95 numerical aperture is used which gives a spread of greater than 70°.

As noted above, after the beam reflects off the surface of the sample it is directed back up through the lens 46 to photodetector 50. The surface of photodetector 50 is shown in cross section in FIG. 3 and in plan in FIG. 4. Photodetector 50 includes a plurality of individual discrete detecting elements the outputs of which can be supplied to processor 52.

In accordance with the subject invention, the detector 50 and processor 52 function to measure the intensity of the reflected probe beam as a function of the angle of incidence of rays within the focused incident probe beam. This result can be appreciated through an optical pathway analysis illustrated in FIGS. 3 and 4. As can be seen, the center element 70 of detector 50 will receive and measure the light intensity of ray 60 passing through the center of lens 46. Accordingly, the output of detector element 70 will correspond to a ray having an angle of incidence of 0°. The radially outer elements 76 A-D on detector 50 receive and measure the light intensity of rays 66A and B which have the greatest angle of incidence. As noted above, this angle of incidence is known based upon the numerical aperture of lens 46. Discrete elements 72 A-D and 74 A-D correspond to angles of incidence between 0° and the highest angle. In the illustrated embodiment elements 74 A-D are located in a manner to receive and measure rays 64A and B having an angle of incidence of 30° while discrete elements 72 A-D are located in a manner to receive and measure rays 62A and B having angle of incidence of 15°.

In the most basic form of the subject invention, information about parameters of the sample can be calculated based on a single angle of incidence measurement. In this case, it is only necessary to take measurements at one radial position within the beam. Thus, for example, if an angle of incidence of 30° is selected, the detector can be limited to having discrete elements at one or more radial locations as illustrated by elements 74. Clearly, if more elements having that radius are provided, the accuracy of the measurement obtained by the system can be enhanced.

Figure 5:
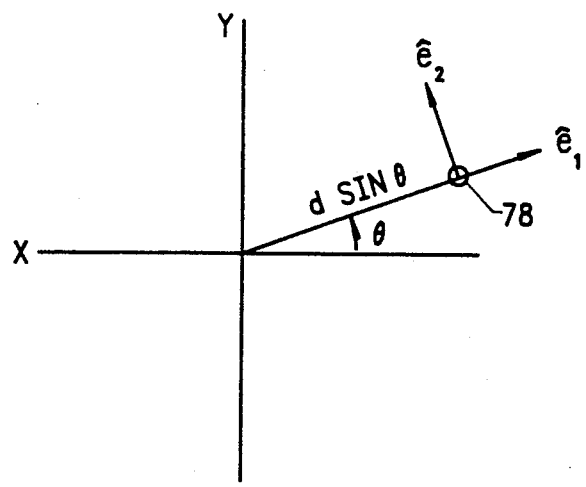
FIG. 5 is a diagram illustrating the relationship between the reflected rays and the photodetector.

The mathematical approach used in analyzing the subject system will be explained below with reference to FIG. 5. FIG. 5 illustrates a coordinate system in the plane of detector 50 which defines the polarization state of a circularly polarized beam incident on the sample. Element 78 represents one detector element located at a point $d \sin \theta$ where d is the working distance of the lens 46 and $\theta$ is the angle of incidence of the reflected ray.

With circularly polarized light $[(E_0(\hat{e}_x + i\hat{e}_y)]$ focused onto a reflecting surface through an objective with a working distance d, the spatially dependent reflected electric field $E_R(\theta, \phi)$ after passing back up through the objective can be written in the form:

$$E_R(\theta, \phi) = E_0 e^{i\phi}[\hat{e}_1 R_p + \hat{e}_2 R_s] \quad (5)$$

where $E_0$ is the amplitude of the incident field, $\hat{e}_1$ and $\hat{e}_2$ are unit vectors along the axes depicted in FIG. 5, $R_p$ is the complex p-wave amplitude reflection coefficient and $R_s$ is the complex s-wave amplitude reflection coefficient. $R_p$ and $R_s$ are functions of the angle $\theta$ and independent of $\phi$.

In terms of the ellipsometric parameters $\psi$ and $\delta$ we have for this reflected field $$E_R = E_0 R_s e^{i\phi}[\hat{e}_1 \tan \psi e^{i\delta} - i\hat{e}_2] \quad (6)$$

where $$\frac{R_p}{R_s} = \left|\frac{R_p}{R_s}\right| e^{i\delta}$$

defines $\delta$ and $$\tan \psi \equiv \left| \frac{R_p}{R_s} \right|.$$

If we pass the reflected beam through a linear polarizer oriented along the x-axis, then the measured signal, $S_x$, is given by:

$$S_x = \tfrac{1}{2} |R_s|^2 [\tan^2 \psi + 1 + (\tan \psi^2 - 1) \cos 2\phi + 2 \tan \psi \sin \delta \sin 2\phi] \quad (7)$$

which is periodic in $2\phi$. This general expression can be simplified if actual measurements are taken at different angles $\phi$. These measurement could be made by rotating the detector so that the angle $\phi$ is changed. As will be discussed below, with reference to the preferred embodiment, the optically equivalent effect can be achieved in a simpler fashion by passing the beam through a rotating polarizer.

In order to derive the first ellipsometric parameter $\psi$, measurements can be taken at $\phi = 0$ and $\phi = \pi/2$. The measured signal at $\phi = 0$ is defined as follows:

$$S_x(0) = |R_s|^2 \tan^2 \psi = |R_p|^2 \quad (8)$$

The measured signal at $\phi = \pi/2$ is given by:

$$S_x(\pi/2) = |R_s|^2 \quad (9)$$

and therefore the value for $\psi$ is $$\tan^2 \psi = \frac{S_x(0)}{S_x(\pi/2)} \quad (10)$$

In order to derive $\delta$, we two additional measurements can be taken at $\phi = \pi/4$ and at $\phi = -\pi/4$. At $\phi = \pi/4$, the measured signal is given by:

$$S_x(\pi/4) = \tfrac{1}{2} |R_s|^2 [\tan^2 \psi + 1 + 2 \tan \psi \sin \delta] \quad (11)$$

and at $\phi = -\pi/4$ the measured signal is given by:

$$S_x(-\pi/4) = \tfrac{1}{2} |R_s|^2 [\tan^2 \psi + 1 - 2 \tan \psi \sin \delta] \quad (12)$$

Taking the difference between equations 11 and 12 we obtain:

$$S_x(\pi/4) - S_x(-\pi/4) = 2|R_s|^2 \tan \psi \sin \delta \quad (13)$$

and taking the sum of equations 11 and 12 we obtain:

$$S_x(\pi/4) + S_x(-\pi/4) = |R_s|^2 [\tan^2 \psi + 1] \quad (14)$$

and consequently $\delta$ can be expressed as:

$$\sin \delta = \frac{S_x(\pi/4) - S_x(-\pi/4)}{S_x(\pi/4) + S_x(-\pi/4)} \left[ \frac{(\tan^2 \psi + 1)}{2 \tan \psi} \right] \quad (15)$$

Since the value for $\psi$ has been obtained with the first two measurements using equation 10, $\delta$ can be calculated using equation 15 and the second two measurements. By using lock in detection and passing the reflected beam through a rotating linear polarizer, highly accurate measurements of the ellipsometric parameters $\psi$ and $\delta$ can be made. In addition, the $\theta$ dependence provides a certain spectroscopic capability due to the variation of optical path length with varying $\theta$ as discussed below.

Figure 6:
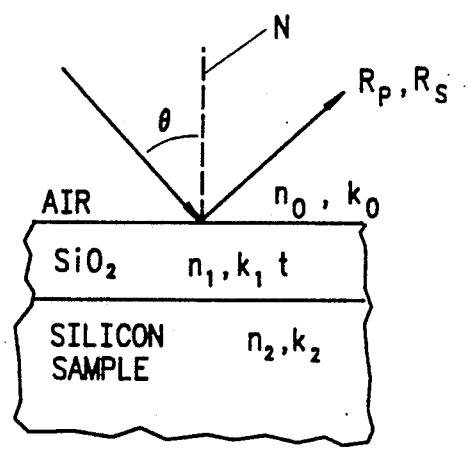
FIG. 6 is a diagram of a test sample defined by a silicon semiconductor wafer having a thin film silicon dioxide layer on the surface.

As noted above, multiple-angle-of-incidence (MAI) measurements is one method of increasing the number of independent ellipsometric measurements. In the Air—$SiO_2$—Si system shown in FIG. 6, for example, there are in general seven parameters that may need to be measured ($n_0$, $k_0$, $n_1$, $t$, $k_1$, $n_2$, $k_2$; where n and k are the real and complex components of the refractive index and t is the film thickness). In practice, $k_0$ and $k_1$ are negligible so that for this system only five parameters must be calculated. However, in a single-angle-of-incidence measurement we obtain only two quantities; $\psi$ and $\delta$, and therefore can measure only two of the five parameters. By varying the angle of incidence $\theta$, additional ellipsometric information is obtained and all five of the parameters in the Air—$SiO_2$—Si system can be measured. For very thin films (less than 100 Å), some care is required in choosing the incident angles in order to obtain independent information and of optimal measurement, the number of angles chosen should be large enough to offset the effects of noise in the data.

In the subject configuration, measurements at different angles of incidence are obtained by detecting rays at different radial positions within the reflected probe beam. The relationship between the location of the detector elements with the angle of incidence of rays within the probe beam with respect to the sample surface is defined during calibration of the instrument. When using a numerical aperture lens of 0.95, angles from 0° to 70° are readily accessible and consequently the ellipsometric information necessary to correctly characterize the Air—$SiO_2$—Si system is available. It should be noted that this full spread of angles is accessible without adjusting the position of the probe beam generating or collecting components.

A difficulty encountered in the traditional MAI ellipsometers is that the measurement of the substrate optical properties becomes increasingly difficult as the film thickness increases (thickness greater than 1000 Å). To overcome this problem, the spectroscopic aspects of the MAI measurements can be utilized. This approach is not true spectroscopy lo since the wavelength of the probe beam is not changing. However, variations do occur in optical phase as the beam passes through the $SiO_2$ layer with varying angles of incidence that is equivalent to changing the wavelength at a fixed angle of incidence. The optical phase $\Phi$ as a function of $\theta$ can be written as $$\Phi(\theta) = \frac{4\pi n_1 t}{\lambda(\theta)} \quad (16)$$

where $$\lambda(\theta) = \frac{\lambda_0}{\sqrt{1 - \left(\frac{n_0}{n_1} \sin \theta_0\right)^2}} \quad (17)$$

and $\lambda_0$ is the fixed wavelength of the laser. At 70° with $n_0 = 1$, $n_1 = 1.46$ $$\lambda(70) = 1.31 \lambda_0 \quad (18)$$

so that with $\lambda_0 = 6328$ Å the effective range of wavelength is between 6328–8290 Å.

Figure 4:
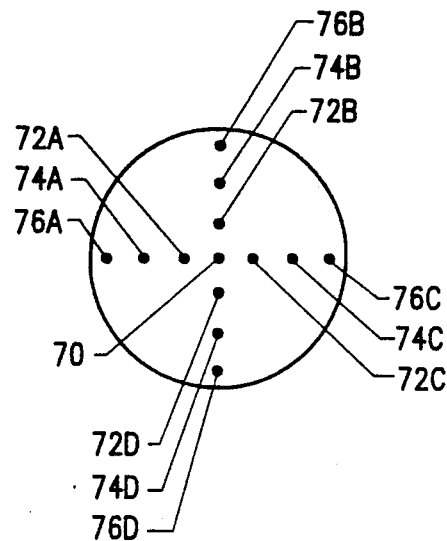
FIG. 4 is a plan view of the surface of a photodetector which can be used to carry out the method of the subject invention.
Figure 7:
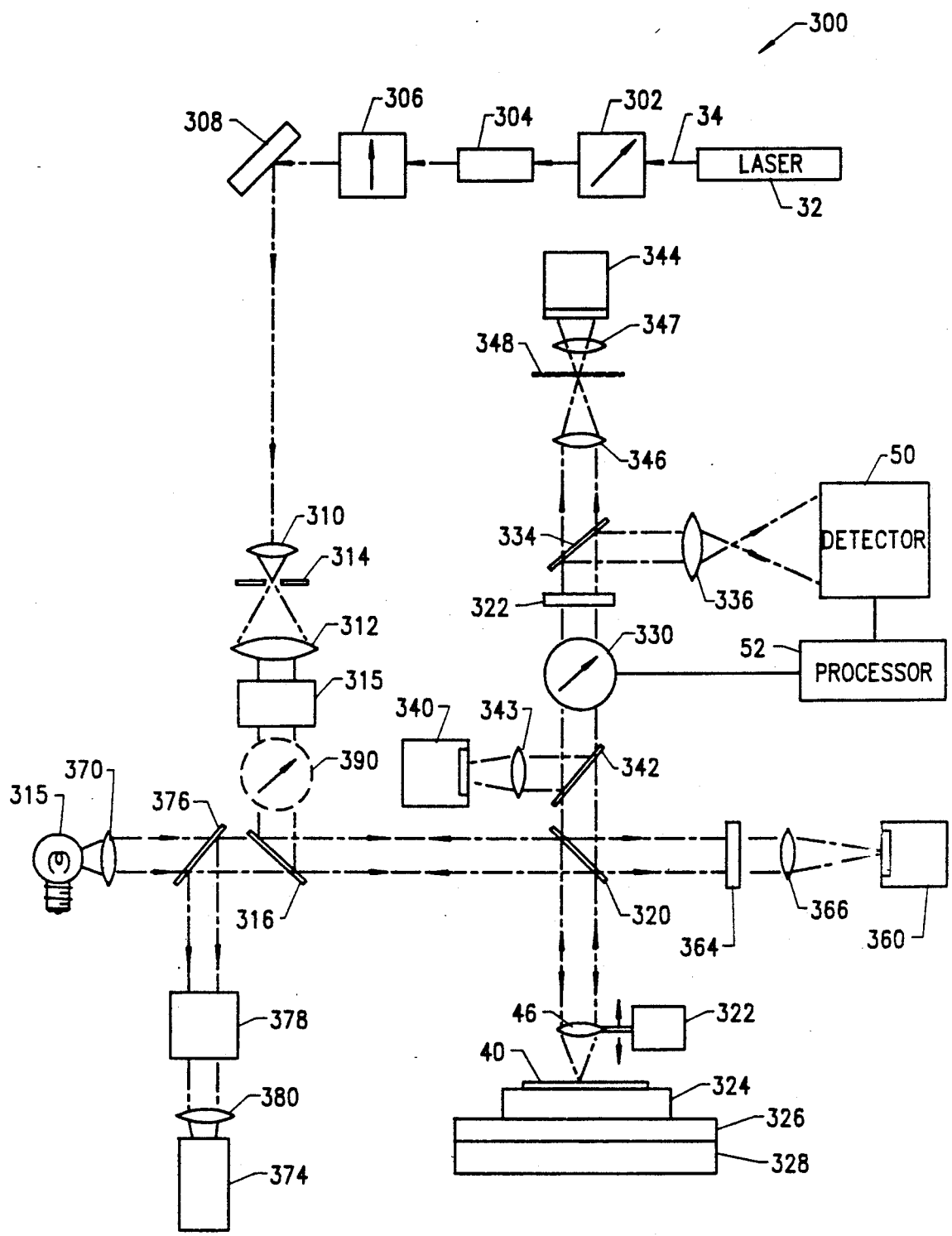
FIG. 7 is a schematic diagram of the preferred embodiment of the subject invention.

Having described the basic theory and operation of the subject's invention, one preferred apparatus 300 for carrying out the measurements will be described with reference to FIG. 7. In FIG. 7, parts equivalent to the structure shown in FIGS. 2 through 4 are numbered the same. FIG. 7 illustrates the optical pathways of the apparatus. It should be noted that the components shown in FIG. 7 herein are quite similar to those described in applicants' prior pending application Ser. No. 07/347,812, filed May 4, 1989. The principle difference is the presence of additional components for varying and isolating the polarization state of the reflected probe beam.

As noted above, laser 32 generates an output beam 34. Laser 32 can be a linearly polarized helium neon laser having a 5 milliwatt power output and a polarization oriented at 45°. Beam 34 could also be generated by a semiconductor diode laser. Beam 34 is passed through a polarizing filter 302 oriented at 45° to insure only 45° polarized light is transmitted. This light is then passed through a faraday rotator 304 for rotating the polarization an additional 45° to prevent spurious reflected helium neon radiation from being reflected back into the helium neon laser. This arrangement reduces instabilities in the power output of the laser caused by spurious reflected HeNe radiation. Beam 34 is then passed through a polarizing filter 306 oriented at 90° to further reduce spurious reflected radiation from going back into the laser.

The beam 34 is then reflected downward by a 95% metallic coated glass turning mirror 308 and into a beam expander/spatial filter arrangement. This arrangement includes an input lens 310 and an output lens 312. A pin-hole filter 314 is provided to improve the beam profile and its uniformity. The beam that exits lens 312 is expanded by the ratio of the focal lengths of lens 310 and lens 312.

In accordance with the subject invention, a component 315 is provided which defines the polarizing section 36 of FIG. 2. In the illustrated embodiment, component 315 is defined by a fixed, birefringent quarter wave plate which converts the linear polarized light into circularly polarized light. This element is often referred to in the ellipsometric texts as the compensator.

The circularly polarized beam 34 is then turned with a metallic coated glass beam splitter 316 having an 20% transmission and 80% reflection. This beam splitter is used to combine the HeNe probe beam and white light from source 318. The white light is used to image the sample using a vision system described in greater detail below.

The probe beam is then directed downward towards the sample by a metallic coated glass beam splitter 320 having a 60% transmission and 40% reflection. This beam splitter also functions to turn the white light down towards the sample. Upon return from the sample, part of the probe beam passes up through the splitter 320 and will be collected by the detector 50. Some of the white light from source 318 will be reflected back to the vision system.

The probe beam is focused on the sample through the objective lens 46. Lens 46 has a high numerical aperture so the various rays in the focused beam will have a wide spread of angles of incidence. In the preferred embodiment, lens 46 has a numerical aperture of 0.95 generating a spread of angles of incidence of greater than 70°. The position of lens 46 is controlled by an autofocus mechanism 322. As noted above, beam 34 is focused to a spot size less than 1 micron in diameter on the surface of sample 40. The sample 40, which may be a silicon semiconductor with a thin film oxide layer, is mounted on a stage which provides X, Y and rotational positional movement. The top stage 324 provides rotational movement as well as a vacuum chuck for holding down the wafer. Stages 326 and 328 provide X and Y linear movement.

Light from the HeNe probe beam and white light that is reflected from the sample passes through beam splitter 320 into the analyzing section of the subject ellipsometer. In the preferred embodiment, the component 330 of the analyzer section is defined by a rotating polarizing filter. Rotating polarizing filter 330 functions to select the polarization axis to be sampled by the detector 50. The polarization orientation selection occurs at twice the rotation rate of the rotating filter.

The continued transmission of white light past filter 330 is restricted by a band pass filter 332 which transmits only the 633 nm HeNe wavelength radiation. A portion of the HeNe probe beam is then redirected by a metallic coated glass beam splitter 334 to beam profile detector 50. Beam splitter 334 has a 20% transmission and an 80% reflection. The reflected light from beam splitter 334 is expanded by lens 336 and imaged on detector 50. Detector 50 can be defined by a diode array, CCD camera, scanning pin-hole or fiber optic sensor array. Preferably, detector 50 has detector elements which are radially positioned in a two-dimensional array in a manner to extract information about reflected rays at specific angles of incidence. The output of detector 50 is supplied to the processor 52. Information about the azimuthal position of rotating polarizing filter 330 is also supplied to the processor. As noted above, the effect of rotating the linear polarizer is optically equivalent to rotating the detector so that the ellipsometric parameters can be derived as discussed above. The actual calculations will depend on the particular polarizing components that are selected.

As mentioned above, the accuracy of the thickness measurement can be further enhanced by measuring the full power of the reflected probe beam. In the embodiment illustrated in FIG. 7, a separate, single cell photodetector 340 is provided for that purpose. A small portion of the probe beam is directed to the detector 340 by metallic coated glass beam splitter 342. A lens 343 can be used to image the full beam onto the surface of the detector 340. In this manner, the probe beam will underfill the detecting surface so that the full power of the beam can be measured.

In the illustrated embodiment, an autofocus mechanism is provided. Autofocus mechanism includes a bicell photodetector 344 and a chopper wheel or moving Foucault knife edge 348. An autofocus lens 346 is provided for focusing the probe beam onto the chopper wheel 348. An autofocus field lens 347 can also be provided. Autofocusing using these types of components is known in the art.

In order to insure proper calibration, the output power of the laser 32 must be monitored. This result is achieved using a detector 360 upon which a part of the probe laser beam 34 is directed. A band pass filter 364 is provided to remove white light from the HeNe probe beam. Lens 366 is used to image the beam onto detector 360.

In the illustrated embodiment, apparatus 300 includes a vision system to allow the operator to locate points on the sample. The vision system includes a white light source 318 and a collimating lens 370. A portion of the white light returning from the sample is directed downward to a camera 374 by a 50/50 beam splitter 376. Some form of filter 378 can be provided to control the amount of HeNe probe beam radiation falling on the video camera. Lens 380 focuses the image of the sample onto the camera.

The basic operation of the apparatus 300 is the same as set forth above with respect to FIGS. 2–4. The detector 50 and processor 52 function to measure the intensity of the reflected probe beam as a function of the angle of incidence of the rays in the incident focused probe beam based on the radial location of the rays within the reflected beam. Multiple angle of incidence measurements can also be taken. Calculations of sample parameters are based on the measured light intensity and the azimuthal position of the rotating polarizing filter. The calculations can be refined by measuring the full power of the reflected probe beam measured by detector 340 in the manner described in applicants prior application Ser. No. 07/347,812.

The preferred embodiment illustrated in FIG. 7 can be easily modified to correspond to other known ellipsometric approaches. For example, the polarizing section can be expanded with the addition of a rotating polarizing filter 390 (shown in phantom). Filter 390 would function to pass only linearly polarized light whose polarization is oriented with the transmission axis of the rotating polarizing filter. The frequency of rotation of the polarization axis is twice the rotation rate of the rotating filter.

As can be appreciated, the preferred embodiment utilizes a photometric ellipsometric approach. It is within the scope of the subject invention to arrange the polarizer and analyzer sections to perform null ellipsometry. It is also within the scope of the subject invention to combine the detector and analyzer sections as taught by U.S. Pat. No. 4,725,145 to Azzam, cited above.

In summary, there has been disclosed a new ellipsometric method and apparatus which provides greatly enhanced spatial resolution. As described above, a probe beam, having a known polarization state, is tightly focused and directed substantially normal to the surface of the sample. The polarization state of the probe beam is analyzed after it interacts with the sample. In addition, the angle of incidence of at least one ray in the reflected probe beam is determined based on the radial position of that ray within the reflected beam. Multiple angle of incidence measurements can be made by using a plurality of rays within the reflected beam at different radial positions.

While the subject invention has been described with reference to the preferred embodiments, various other changes and modifications could be made therein by one skilled in the art without varying from the scope or spirit of the subject invention as defined by the appended claims.

We claim:

1. An ellipsometric apparatus for use with a sample comprising:

means for generating and directing a probe beam of radiation, of a known polarization state, substantially normal to the surface of the sample;

means for focusing the probe beam such that various rays of said focused probe beam create a spread of angles of incidence with respect to the sample surface; and means for analyzing the polarization state of at least one ray in the probe beam after it has interacted with the sample, said means further functioning to determine the angle of incidence with respect to the surface of the sample of said one ray based on the position of the ray in said probe beam.

2. An apparatus as recited in claim 1 further including a processor means for evaluating parameters of the sample based on the polarization state detected by said analyzing means of rays of at least one angle of incidence with respect to the surface of the sample.

3. An apparatus as recited in claim 2 wherein said processor means evaluates said sample parameters based on the polarization state of rays corresponding to a plurality of angles of incidence with respect to the surface of the sample.

4. An apparatus as recited in claim 1 wherein the angle of incidence with respect to the surface of the sample of said one ray is determined by its radial position with said probe beam.

5. An ellipsometric apparatus for use with a sample comprising:

means for generating and directing a probe beam of radiation substantially normal to the surface of the sample;

means for polarizing said probe beam;

means for focusing the probe beam such that various rays of said focused probe beam create a spread of angles of incidence with respect to the sample surface; and means for analyzing the polarization state of at least one ray in the probe beam after it has interacted with the sample, said means further functioning to determine the angle of incidence with respect to the surface of the sample of said one ray based on the position of the ray in said probe beam.

6. An apparatus as recited in claim 5 wherein said analyzer means includes a detector for measuring the intensity of at least one ray of the probe beam whereby in operation said polarizing and analyzing means are adjusted so that the intensity of that probe beam ray reaching the detector is varied.

7. An apparatus as recited in claim 5 wherein said polarizing and analyzing means are rotatable about an azimuthal angle with respect to the surface of the sample, said polarizing and analyzing means being rotated in order to vary the intensity of that probe beam ray reaching the detector.

8. An apparatus as recited in claim 7 wherein polarizing and analyzing means are adjusted to minimize the intensity of the probe beam ray reaching the detector.

9. An apparatus as recited in claim 5 wherein said polarizing means includes a linear polarizer and a compensator to create elliptically polarized radiation having a known polarization state and wherein said analyzing means includes a rotatable analyzer for detecting the linear polarization components in the probe beam.

10. An apparatus as recited in claim 5 wherein said focusing means creates a spread of angles of incidence, from the center ray to the outermost ray, of at least 30 degrees.

11. An apparatus as recited in claim 5 wherein said focusing means is a lens having a numerical aperture of at least 0.5.

12. An apparatus as recited in claim 5 wherein said probe beam is focused to a spot size of about one micron or less in diameter on the surface of the sample.

13. An apparatus as recited in claim 5 further including a processor means for evaluating parameters of the sample based on the polarization state detected by said analyzing means of rays of at least one angle of incidence with respect to the surface of the sample.

14. An apparatus as recited in claim 13 wherein said processor means evaluates said sample parameters based on the polarization state of rays corresponding to a plurality of angles of incidence with respect to the surface of the sample.

15. An apparatus as recited in claim 13 further including a means for detecting the full power of the reflected probe beam and wherein said processor means derives information about the parameters of the sample based upon both the polarization state of a ray in the reflected beam at a known angle of incidence and the full power of the reflected probe beam.

16. An apparatus as recited in claim 5 wherein the angle of incidence with respect to the surface of the sample of said one ray is determined by its radial position with said probe beam.

17. An apparatus as recited in claim 16 wherein said analyzing means includes a detector having an array of sensing elements located at differential radial positions, each said sensing element generating a signal proportional to the light intensity falling thereon, and with the radial position of said elements corresponding to specific angles of incidence with respect to the surface of the sample of rays within the reflected probe beam.

18. An ellipsometric method of use with a sample comprising the steps of:

focusing a probe beam of radiation, having a known polarization state, substantially normal to the surface of the sample to create a spread of angles of incidence with respect to the sample surface; and analyzing the polarization state of at least one ray in the probe beam after it has interacted with the sample and determining the angle of incidence with respect to the surface of the sample of said one ray based on the position of the ray in said probe beam.

19. A method as recited in claim 18 further including the step of evaluating parameters of the sample based on the polarization state and angle of incidence of said one ray.

20. A method as recited in claim 19 further including the step of evaluating parameters of the sample based on the polarization state of rays corresponding to a plurality of angles of incidence with respect to the surface of the sample.

21. A method as recited in claim 18 further in the step of detecting the full power of the reflected probe beam and wherein the step of evaluating further includes deriving information about the parameters of the sample based upon both the polarization state of a ray in the reflected beam at a known angle of incidence and the full power of the reflected probe beam.

22. A method as recited in claim 18 wherein said spread of angles of incidence of said focused probe beam is at least 30 degrees from the center ray to the outermost ray.

23. A method as recited in claim 18 wherein the probe beam is focused to a spot size of about one micron or less in diameter on the surface of the sample.

24. An apparatus as recited in claim 18 wherein the angle of incidence with respect to the surface of the sample of said one ray is determined by its radial position with said probe beam.

* * * * *